United States Patent
Jessop

(12) 
(10) Patent No.: US 6,324,916 B1
(45) Date of Patent: Dec. 4, 2001

(54) TESTING SHEAR BOND STRENGTH

(75) Inventor: Neil T. Jessop, Colton, CA (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 09/467,665

(22) Filed: Dec. 15, 1999

(51) Int. Cl.[7] .................................................. G01N 3/24
(52) U.S. Cl. .............................................. 73/842; 73/841
(58) Field of Search ...................................... 73/841, 842

(56) References Cited

PUBLICATIONS

McFadden et al. Effects of disinfectants on shear bond strenghts of two dentin bonding systems. Feb. 1997. http://dentisty.llu.edu/biomat/mcfadden/mcfadden.html.

Rock et al. Shear bond strenths produced by composite and compomer light cured orthodontic adhesives. 1997. Journal of Dentistry. vol. 25, 3–4, p. 243–49.

Asmussen et al. Stiffness, elastic limit, and strength of newer types of endodontic posts. 1999. Journal of Dentistry. vol. 27, 4, p. 275–78.

Shahdad, S.A. Bond strenght of repaired anterior composite resins: an in vitro study. 1998. Journal of Dentistry. vol. 26, 8, p. 685–94.

Curtis, R.V. Stress–strain and thermal expansion characteristics of a phosphate–bonded investment mould material for dential super plastic forming. 1998. Journal of Dentistry. vol. 26, 3, p. 251–8.*

"Danville Engineering: Pioneer In Air Abrasion Technology" http://www.danvilleengineering.com.

"User Instruction Guide: Embedding Teeth Or Relevant Objects As Specimens" http://www.edoc.co.za/dentalnet/research/microgrip/bencor.shtml.

* cited by examiner

Primary Examiner—Benjamin R. Fuller
Assistant Examiner—Lilybett Martir
(74) Attorney, Agent, or Firm—Workman, Nydegger & Seeley

(57) ABSTRACT

The present invention provides an apparatus and a method to apply a load to an adherend, which is bonded to a substrate, to allow an accurate measurement of the bond between an adherend and substrate. The strength of the bond is tested by shearing the adherend from the substrate and measuring the force per unit area required to fail the bond. This is accomplished by positioning a crosshead at the base of the adherend and applying a load, which is parallel to the surface of the substrate against the base of the adherend. The strength of the bond is the force per unit area required to shear the adherend from the substrate. The accuracy of the measurement is enhanced by minimizing the surface area of the crosshead that is in contact with the substrate and by ensuring that the adherend is not fractured during testing. Fracturing and deformation of the adherend is limited by using a notch to test with rather than a straight chisel. The present invention is configured to load the adherend such that the strength of the bond may be measured accurately.

18 Claims, 12 Drawing Sheets

TESTING SHEAR BOND STRENGTH

BACKGROUND OF THE INVENTION

1. The Field of the Invention

The present invention relates to a device that is used to test the bond strength of an adherend, which is formed from a hardenable material, and is bonded to a test piece. More particularly, the present invention is related to testing bond strength between an adherend and a substrate by shearing the adherend from the substrate.

2. The Prior State of the Art

The goal of forming a bond between restorative dental materials and dentin, enamel, or other dental substrates is to withstand the significant shear forces created in the oral environment and to reinforce the remaining tooth structure. For this reason, high bond strengths are desirable. Measuring the strength of a bond between restorative dental materials and dental substrates requires two steps. First, the bond between the dental materials must be formed and second, the restorative dental material must be sheared or pulled until failure occurs and then the peak force per unit area is determined.

The formation of a bond has several steps. First, the type of dental substrate, adhesive and adherend to be tested are selected. If the dental substrate is irregularly shaped, such as a tooth, then the tooth is mounted in resin to form a bonding substrate test piece. The test piece is cut or polished to create a smooth, flat top surface with a portion of the tooth exposed, preferably at the same level as the resin. The exposed portion of the tooth or other dental substrate is referred to herein as a test sample. Next, the top surface of the test sample is etched and typically rinsed to remove any contaminates. The test sample, or at least a portion thereof which will be the bond site, is then coated with a primer and/or adhesive, which will either be light cured or be allowed to chemical cure. A secondary restorative dental material (adherend) is then placed on the bond test site and is also light cured or chemical cured. The curing process hardens both the adhesives and the adherend. Once this process is completed, a bond has been formed between the restorative dental materials and the test sample or dental substrate such that a bond assembly now exists. The process of creating the bond assembly in the prior art presents several problems, which prevent the strength of the bond from being accurately measured.

The first problem associated with the bond assembly is related to the shape of the adherend. A cylindrical shaped adherend is the most conducive for obtaining an accurate measurement of the bond strength. Any other geometric shape, as well as deviations in the cylindrical shape lead to less accurate measurements of bond strengths. A perfect cylindrical shape however, has proven difficult to form as illustrated by the prior art. If the adherend is not formed to have a uniform cross-sectional shape as taken along its length, then a shear device used to shear the adherend for bond strength testing may not be able to properly interface with the adherend.

One prior art method involves bonding a composite filled gelatin capsule onto a testing substrate. In this method, a slightly overfilled gelatin capsule is overturned and manually or mechanically held in place on the substrate. The resulting adherend has a number of problems. First, a manually or mechanically held gelatin capsule is to some extent compressed. This compression deforms the cylindrical shape of the adherend. The second problem is that the gelatin capsule must be held immobile during the hardening process, which is difficult to do manually. This factor further deforms the shape of the composite material. The third problem is that the gelatin capsule must be slightly overfilled to ensure the proper adaptation of the composite to the substrate. When the composite filled capsule is placed onto the substrate the excess composite must be removed before curing takes place. This process creates difficulty in keeping the capsule stationary before curing which leads to further deformation. The combination of these deforming factors produces a composite material that is not perfectly cylindrically shaped and will not fit a shear device perfectly, which results in inaccurate bond strength measurements. A further difficulty is ensuring that the gelatin capsules are held perpendicularly to the dentin. If the adherend is not perpendicular to the substrate then the test loads will not be able to be applied properly.

Another attempt to eliminate these problems is the use of a small stainless steel nozzle, which is attachable to a guide fixture. The nozzle has small windows through which composite material can be added and through which the composite material is light cured. This method eliminates deformities in the shape of the composite material due to compression. However, it still has problems because the small windows cause difficulty in composite placement and curing. The windows limit the amount of light that can enter the nozzle to cure the composite material, which leads to inaccurate measurements of the bond strength because the composite material may not be completely cured. Removing the nozzle, after the curing process is difficult because the cured composite often extends into the windows, thus binding the nozzle in place. The difficulty in removing the nozzle creates stress on the newly formed bond and can weaken or fracture the bond. Note, the nozzle is held perpendicular to the substrate by means of a guide fixture, which also limits the user in choosing a suitable test site. Additionally, the stainless steel mold will not allow use of some restorative materials such as glass ionomers, copolymers, luting cements, and amalgam, thus limiting the ability to gather information related to such dental restorative materials. An example of such stainless steel instruments is the system sold under the name Bencor Multi-T. Information regarding this system is provided by a distributor, Danville Engineering at "www.danvilleengineering.com" which is linked to "www.edoc.co.za/dentalnet/research/microgrip/bencor.shtml" to provide more detailed information.

The next problem in the prior art is that the bond is not limited to the area between the test site and the adherend. When adhesives are applied to the substrate, it is typically applied to the entire surface of the substrate. This excess adhesive is not removed before the curing process occurs and results in a resin snowshoe or shelf, which encompasses more surface area than the test site. This resin snowshoe can distribute test loads out over the surface of the substrate; similar to the way a snowshoe spreads out the load of a human over a broader area. This resin snowshoe prevents the true strength of the bond from being measured. In essence the resin snowshoe bonds the adherend to more than just the test site. For this reason, the measurement of the bond strength is not accurate. The use of split molds, straws, or tubing such as TYGON™ tubing to create an adherend without creating a "resin snowshoe" requires the application of the primer and adhesive through the openings of these devices. When adhesives are applied in such a manner, capillary action occurs and some of the adhesive is drawn up the interior walls. Since this negatively influences the accuracy of test data, the result is inaccurate measurement of material properties.

Once the bond is formed between the substrate and the adherend, the strength of the bond can be tested. Testing the bond strength means measuring the force per unit area required to shear the adherend from the substrate. In addition to the factors related to the formation of the bond that effect test results, the actual testing of the bond could introduce inaccuracies. The prior art demonstrates additional problems that can influence the measurement of the bond strength.

The frictional force between the shear device and the test piece must be taken into account in order to obtain accurate bond strength measurement. The frictional force is typically greater when the shear device has a large amount of surface area in contact with the surface of the test piece or is held in place with guide fixtures. The shear device must load the bonded specimen until the adhesive fails without fracturing the adherend. If the adherend fractures first, then the adhesive is not the reason for failure and an accurate bond strength measurement cannot be obtained. The problem with fracturing the adherend rather than shearing the adhesive is more prominent when the adherend is not perpendicular to the substrate. If the shear device is too thin, then the adherend is, once again, more likely to be fractured and the resulting bond strength measurement is resultantly inaccurate. The shear force must be applied as close to the bond interface as possible or at the base of the adherend. If the shear force is not applied at the base of the adherend, a lever arm will be created and the force required to shear the bond will be measured inaccurately.

There are other methods of creating bond assemblies which maintain the controls necessary to obtain fairly accurate measurements but they are very cumbersome to use which limits productivity. These prior art systems do not offer the user ease of use, freedom of material choice, and choice of bond location while still maintaining the accuracy needed.

Researchers are employing many different methods of testing shear bond strength. Many of the methods involve complex fixturing which usually introduce more errors than benefits. An example of a method that involves complex fixturing is the method developed by Larry Watanabe, which is identified as ISO TR 11405.

There is a need in the industry for a method for both creating a bond assembly and testing the bond between adherend and the substrate such that the measurements of the bond strength actually represent the bond strengths.

SUMMARY OF THE INVENTION

The present invention addresses the problems in the prior art by creating a bond assembly and testing the bond between a substrate and an adherend. The bond assembly is shaped and formed such that it will yield accurate bond strength measurements upon being tested. Typically, the bonding substrate is dentin, enamel, metal, porcelain, or composite and the adherend is a composite, copolymer, glass ionomer, unfilled resin, or amalgam material.

The present invention shapes the adherend into a cylindrical shape without the deformities caused from being hand held. The cylindrical shape is important, as this shape results in the most accurate measurements of shear bond strength. The invention also permits the light cure restorative materials to be completely cured by providing easy access to the uncured restorative composite material. Additionally, in light cure and chemical cure situations, excess primer or adhesive is prevented from being exposed to the curing light, thereby eliminating the formation of a "resin snowshoe." As a result, the bond to be tested only encompasses the surface area under the adherend, which is the bond site. The present invention forms an adherend that can be completely hardened from exposure to high intensity light, is perpendicular to the substrate, and is uniformly cylindrical in shape.

The present invention allows for accurate measurements of the strength of a bond between an adherend and a substrate to be obtained by shearing the adherend from the substrate with a unique shear device or a crosshead, as disclosed herein below. An accurate measurement of the bond strength is obtained, in part, as a result of the reduced frictional force between the crosshead and a bonding substrate. The frictional force is reduced when compared with other testing systems as the surface area of the crosshead that comes in contact with the substrate is minimal.

The crosshead shears the adherend from the bonding substrate by applying a force that is parallel to the substrate and is directed at the base of the adherend, which is at the site of the bond. By pushing at the base of the adherend with the proper crosshead, the force measured is the shear force required to cause the bond to fail unless fractures occur in the adherend first. Applying a force at a point higher on the adherend is more likely to break the adherend due to leverage, rather than cause the adhesive between the substrate and the adherend to fail. The present invention further enhances the accuracy of the measurement of the bond strength by having a minimal amount of contact between the substrate and the crosshead and by ensuring that the adherend is not fractured off of the substrate or deformed.

Additional objects and advantages of the invention will be set forth in the description, which follows and in part will be obvious from the description, or may be learned by the practice of the invention. The objects and advantages of the invention may be realized and obtained by means of the instruments and combinations particularly pointed out in the appended claims. These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings as listed herein below.

DETAILED DESCRIPTION OF THE PREFERRED EMBODIMENTS

The present invention is directed to methods and apparatus for forming a bonding assembly as well as methods and apparatus for testing the strength of a bond between an adherend and a substrate. FIGS. 1 through 6 illustrate an exemplary embodiment of the components needed to form an adherend and bond the adherend to a bond site of a test piece. FIGS. 1 through 6 are also employed to describe an exemplary method of forming an adherend and bonding the adherend to a bond site of a test piece. FIGS. 7 through 11 illustrate an exemplary embodiment of an apparatus and a method used to test the strength of a bond between an adherend and a bond site of a test piece. FIGS. 12 through 16 depict another embodiment of an apparatus and a method used to test the strength of a bond between an adherend and a bond site of a test piece. Please note that while the methods and apparatus are particularly useful with dental substrates and dental restorative materials, the methods and apparatus may also be utilized with other substrates and adherends.

Figure 1:
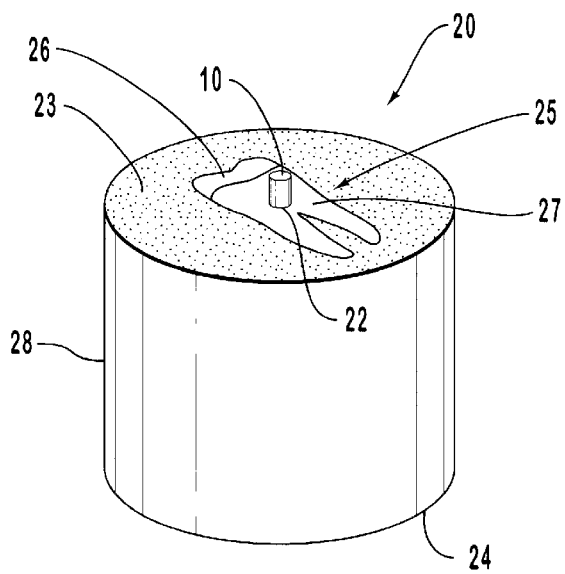
FIG. 1 is a perspective view of a test piece with an adherend bonded to a test sample embedded in the test piece.

FIG. 1 is a perspective view of test piece 20 after adherend 10 and a test bond have been formed. Adherend 10, which is discussed in greater detail herein below, is typically formed from resins that have cured or hardened such as composite resins, glass ionomer, or combinations thereof known as compomers and also from amalgam material. Test piece 20 and its components are discussed first in relation to FIG. 1 to better understand the methods and components illustrated in later figures. Adherend 10 is bonded on a bond site 22 which is a specific portion of test piece 20 identified in conjunction with a molding platform 30 discussed in detail herein below with reference to FIGS. 2–6.

As depicted in FIG. 1, test piece 20 has a top surface 23 opposite a bottom surface 24. Top surface 23 is preferably flat and smooth, as shown, to provide for consistent testing. While bottom surface 24 is preferably flat and parallel, as shown, it can have any shape which enables the top surface to have a desired orientation.

The test piece is shown at 20 as being formed from two components, a tooth shown at 25 and a holding material 28. When it is desired to test the bond strengths for adherends to substrates which are naturally irregularly shaped, such as teeth, it is preferable to form a test piece by at least partially encasing the substrate in a holding material. The holding material may be any suitable resinous material such as various methacrylates. After the irregular shaped substrate is encased or embedded in the holding material and the holding material has been allowed to harden, then both the irregularly shaped substrate and the holding material are shaped until both are substantially smooth and flat. The smooth and flat configurations may be achieved by any suitable method such as grinding. Together the smoothed and flattened substrate and holding material form the top surface of the test piece. Note that, as indicated in the Background section herein above, substrates having irregular shapes, such as teeth, which have been flattened after being embedded in a holding material to produce a two-component test piece are referred to herein as test samples.

While test piece 20 is shown in FIG. 1 as having two separate components, tooth 25 and holding material 28, the present invention can also be utilized with test pieces which are formed from only one material such as porcelain, a particular metal, metal alloys and amalgams, or a composite material. Since materials such as porcelain or metals can be easily formed to have opposing flat surfaces and be sized for easy handling, it may be useful to form such materials into a solid, single component test piece.

Whether the test piece is formed from two components or a single component, the portion of the test piece under the adherend is the bond site. If the test piece includes a test material such as a tooth, as in FIG. 1, then the bond site is the portion of the test material under the adherend as shown at 22. More particularly, the potential bond site may be any part of the test material while the actual bond site is the portion of the test material under the adherend. The dimensions of the bond site are determined, as described in greater detail herein below, by the structure which forms the adherend.

Tooth 25 is positioned on its side such that a small amount of enamel 26 is exposed while exposing as much dentin 27 as possible. The large surface area of dentin combined with the relatively small surface area of enamel enables the adherend to be bonded to the dentin without contacting the enamel. This is particularly desirable since many restorative dental materials are bonded only to dentin. Since it is easier to bond to enamel than to dentin, the bond site preferably includes only dentin when testing the bond strength of restorative materials intended for use with dentin as contact with enamel may provide an inaccurate indicator of bond strength. Accordingly, any portion of dentin 27 which enables adherend 10 to be on dentin without being over enamel is a potential bond site; however, the actual bond site is essentially only the portion of the dentin under the adherend. As described below, the apparatus and systems disclosed herein can be configured to be particularly useful for testing bond strengths of adherends to most dental materials.

Figure 2:
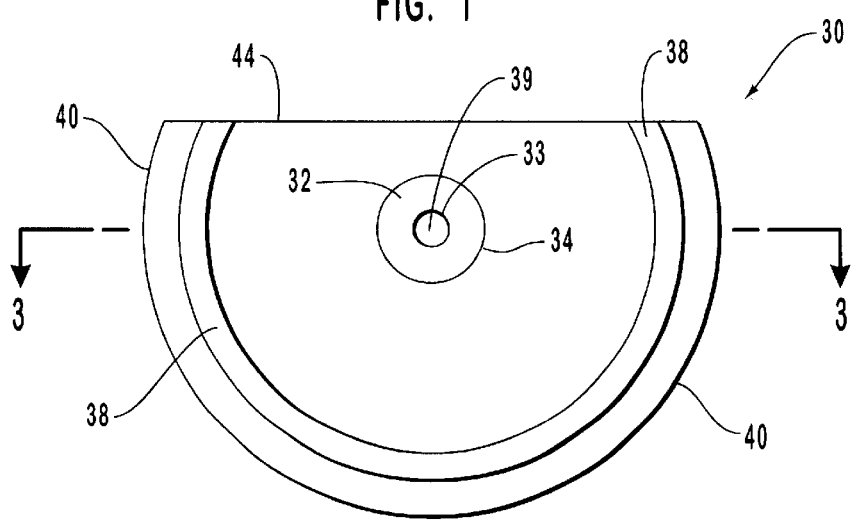
FIG. 2 is a bottom view of a bonding and molding platform.
Figure 3:
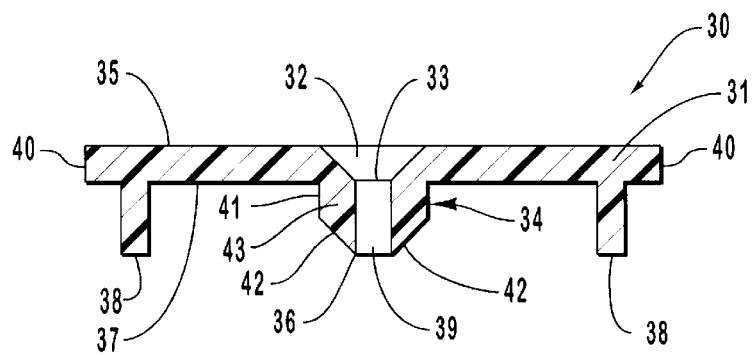
FIG. 3 is a cross-sectional view of the bonding and molding platform in FIG. 2 taken along section line 3—3 of FIG. 2.

FIG. 2 is a bottom view of a bonding and molding platform 30 and FIG. 3 is a cross sectional view of platform 30 taken along the section line 3—3 of FIG. 2. Platform 30 is used to form adherend 10, as shown in FIG. 1, such that adherend 10 is bonded perpendicularly to bond site 22 of the test piece substrate 20. The method of forming adherend 10 and the method of bonding adherend 10 to the substrate 26 or 27 are mentioned in reference to FIGS. 2 and 3, but are more fully discussed in reference to FIGS. 5 and 6.

Platform 30, as shown in FIGS. 2–6, comprises body 31 having top surface 35 opposite a bottom surface 37. Platform 30 has a mold 34 extending downward from bottom surface 37. Platform 30 also has a perimeter support member 38 extending down from bottom surface 37. Preferably, perimeter support member 38 is inset from perimeter 40. Platform 30, as described in relation to FIGS. 2–6, is an example of bonding means for receiving a hardenable material and for enabling light energy to be directed to the hardenable material to yield an adherend on a test piece.

As shown best in FIG. 3, mold 34 is an integral portion of platform 30. Mold 34 has a top end 41 opposite an outlet end 42. A conduit 39 extends through from top end 41 to outlet end 42. Conduit 39 is accessed via portal 33 which is centrally located in countersunk portion 32 of top surface 35. While portal 33 is the inlet opening into conduit 39 the outlet opening is defined by outlet rim 36.

The primary function of mold 34, and particularly conduit 39, is to form and shape an adherend as shown in FIG. 1 at 10. Mold 34 is an example of molding means for forming an adherend on a bond site of a test piece from a hardenable material delivered into the molding means.

Adherend 10 is formed by filling conduit 39 through portal 33 with a hardenable material, such as composite material. The configuration of countersunk portion 32, located in top surface 35 of platform 30, enables conduit 39 to be easily filled with a hardenable material. After conduit 39 is filled with a hardenable material, any hardenable material remaining in countersunk portion 32 is removed.

When the hardenable material in mold 34 is hardened with light irradiation or allowed to chemical cure, adherend 10 is formed. In other words, adherend 10 is a hardenable material that has been cured while inside of conduit 39. Mold 34, more specifically, conduit 39, is designed to properly shape the hardenable material. Accordingly, conduit 39 is preferably cylindrical in shape but may also embody other shapes and conduit 39 preferably has a uniform diameter along its length. Since the hardenable material takes the shape of conduit 39, the cylindrical shape of the conduit yields a cylindrically shaped adherend 10. Not only does conduit 39 ensure that adherend 10 is substantially cylindrical, it also ensures that adherend 10 is substantially perpendicular to top surface 23 of test piece 20.

The depth of mold 34, more particularly, the depth of conduit 39, is sufficient to permit complete cure by light irradiation. The preferred length is in a range from about 1 mm to about 3 mm and the range is more preferably from about 1 mm to about 2 mm.

The width of the conduit and the resulting adherend varies depending on the particular materials to be tested. While any width may be used, the width may, for example range from about 1 mm to about 5 mm. However, less force is required in testing when a smaller diameter is used. Additionally, when testing the shear bond strength on dentin use of a smaller diameter reduces the likelihood of bonding onto enamel. A diameter of about 2.5 mm has been found useful in bonding on dentin without bonding to enamel. Further, for ease in calculating the force required to shear the adherend in Pascals, the diameter is preferably 2.3798 mm.

Conduit 39, which is essentially the inner surface of mold 34 has a diameter which is the same throughout its length. While the exterior surface of mold wall 43 may have a portion which is parallel to conduit 39, as shown at top end 41, the thickness of mold wall 43 of mold 34, particularly in the region of outlet end 42, decreases. The thickness of mold wall 43 decreases until conduit 39 and the exterior surface of mold wall 43 meet to form a point at outlet end 42, which is outlet rim 36. Stated otherwise, outlet end 42 is cone shaped and tapers downward and inward toward conduit 39 such that conduit 39 has a thin circular outlet rim. Since outlet rim 36 is where conduit 39 and the exterior wall of the mold come together or coterminate, it should be understood that outlet rim 36 is integral with and defined by both conduit 39 and the exterior surface of mold wall 43. The advantages of the thin configuration of outlet rim 36 are discussed below in reference to FIG. 5 and FIG. 6.

The function of perimeter 40 and perimeter support member 38 are also best understood, as described herein below, in reference to FIGS. 5 and 6. Perimeter 40 is designed to removably mate with a device that will hold platform 30 immobile while adherend 10 is formed and bonded to bond site 22 of test piece 20. Perimeter support member 38 is designed to withstand the pressure of the device which holds platform 30 such that the shape of mold 34 is not changed, but remains cylindrical while adherend 10 is formed and bonded to bond site 22.

In FIGS. 2–6, platform 30 is shown having a portion cut off to form front 44. Front 44 is designed to facilitate visual access to mold 34 and bond site 22 as adherend 10 is being formed. Front 44 facilitates the alignment of mold 34 over the test piece 20 so that the mold is over the desired bond site. More particularly, by minimizing the distance between the perimeter of the platform and the mold it is easier to see the position of the mold over the test piece to select the location of the bond site. This is particularly important when testing the strength of an adherend on dentin of a tooth embedded in a holding material without contacting enamel.

While the platform is shown in FIGS. 2–6 as having an essentially circular perimeter with a portion cut away to yield a front for visual access, the platform may of course have any shape such as a circle or a square. The preferred shape and embodiment of platform 30 is as described in reference to FIGS. 2–6. Additionally, when the platform has a circular perimeter, the mold can be concentrically or eccentrically located. Similarly, if the platform is noncircular, the mold can be centered or offset.

Figure 4:
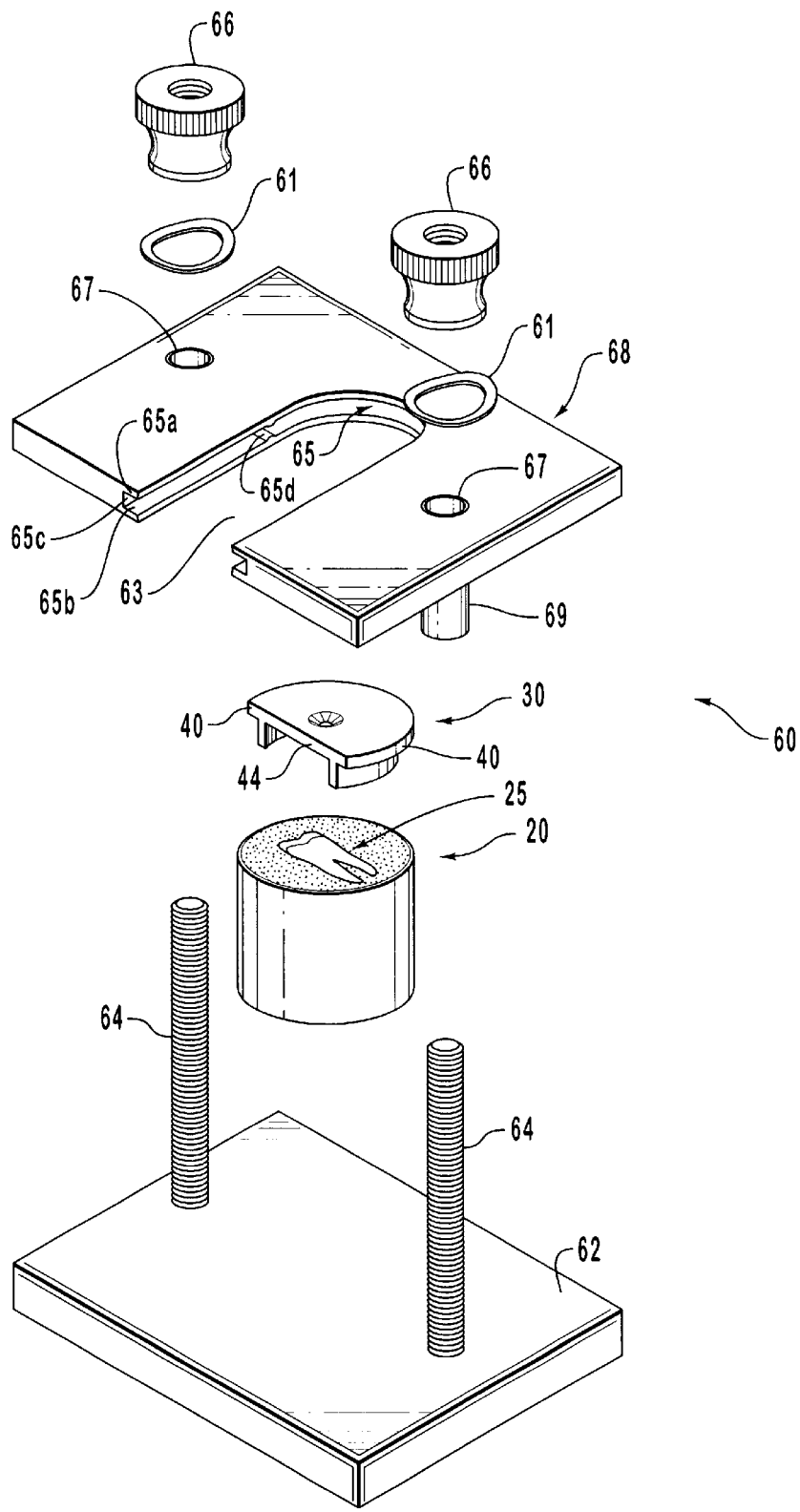
FIG. 4 is an expanded perspective view of the clamping assembly, the bonding and molding platform and the test piece.
Figure 5:
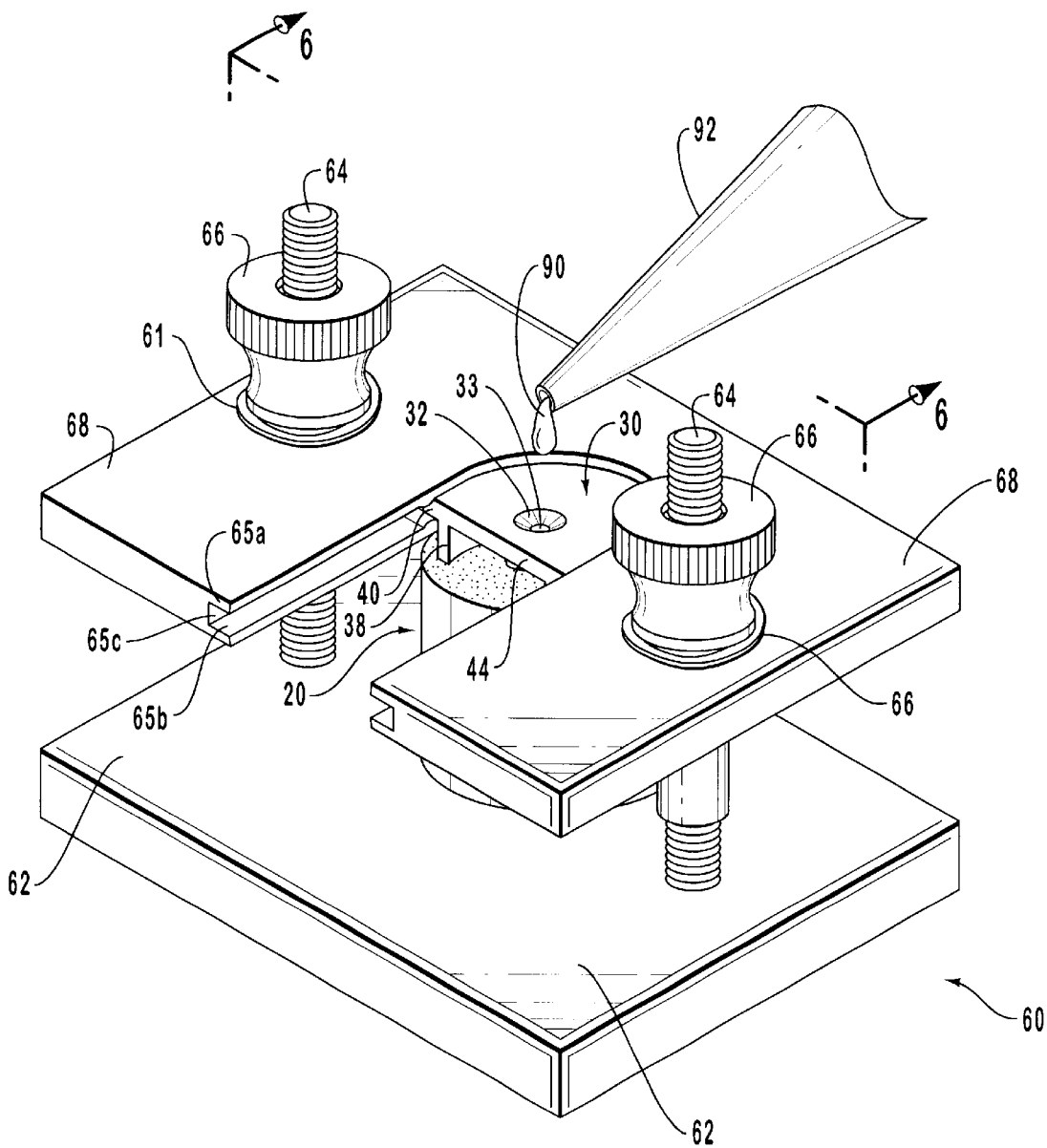
FIG. 5 is a perspective view of the clamping assembly, the test piece, and the bonding and molding platform configured to receive a hardenable material to form an adherend.
Figure 6:
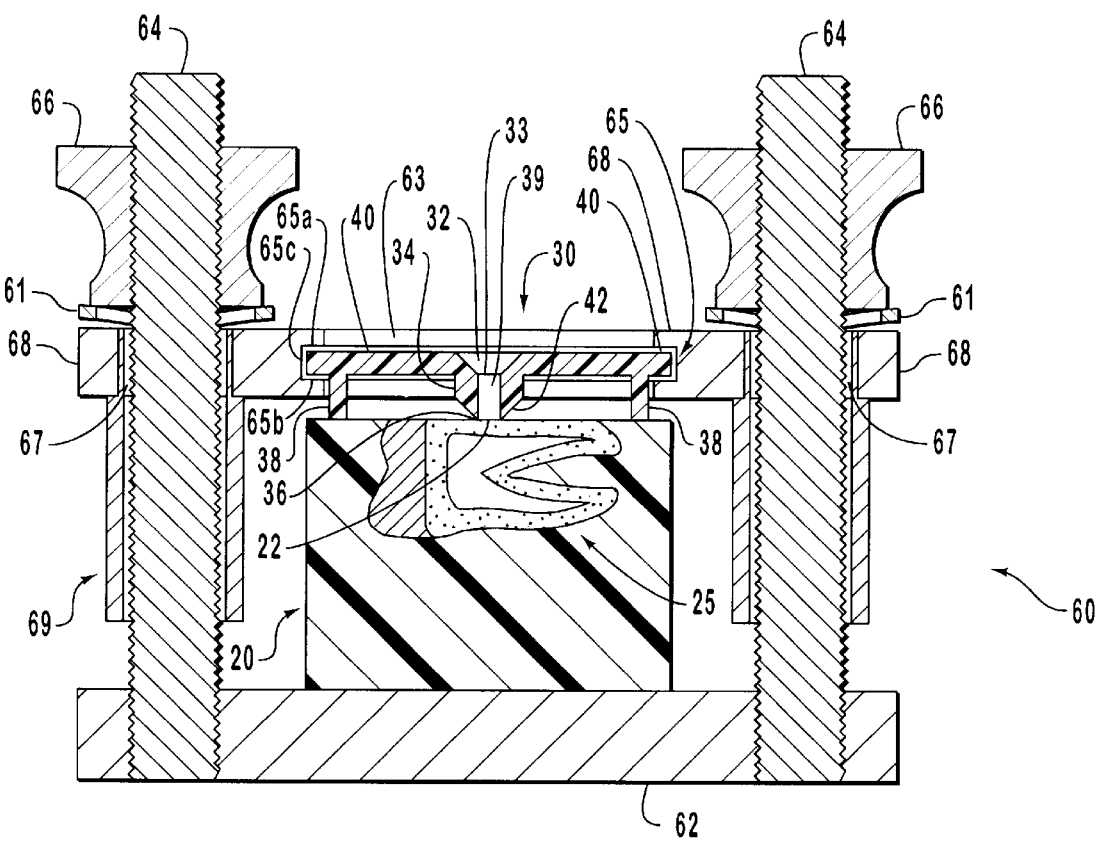
FIG. 6 is a perspective view of FIG. 5 taken along the section line 6—6 of FIG. 5.

FIGS. 4–6 depict a clamping assembly 60 which is a device used to hold platform 30 relatively immobile during formation of adherend 10. The clamping assembly is first described in reference to FIG. 4 which provides an expanded perspective view of test piece 20, platform 30 and clamping assembly 60. The procedures for forming an adherend with platform 30 and clamping assembly 60 are described primarily in reference to FIGS. 5–6, as are the functions and advantages of some of the features of platform 30.

Clamping assembly 60 comprises base 62, posts 64, plate 68 and retention nuts 66. Clamping assembly 60 also preferably includes disc springs 61 and guide bushings 69. Base 62, in the depicted embodiment, is rectangular and has two permanently attached, upward extending posts 64. Plate 68 has two similar apertures 67 on each side of plate 68. Each aperture 67 has a guide bushing 69 press fit into it which is configured to removably mate with post 64 as plate 68 is mounted. Guide bushings may also alternatively be integrally connected to plate 68 and extend downward around each aperture such each post 64 extends through both a guide bushing and an aperture when the plate is mounted. Additionally, in a less preferred embodiment, a plate may be utilized without guide bushings. Each retention nut 66 is configured to removably mate with each respective post 64 to secure plate 68. Posts 64 and retention nuts 66 are preferably threaded, as shown, such that each retention nut 66 can securely and removably mate with each post 64. Disc springs 61 are designed to fit freely on posts 64 such that when retention nuts 66 are tightened against springs 61 a consistent load is applied to plate 68 and in turn to bonding platform 30. Retention nuts 66 may be tightened and loosed such that plate 68 is securely and removably connected to base 62. Clamping assembly 60 is an example of means for holding a platform and a test piece in a fixed position with respect to each other while adherend is formed and bonded to the substrate, such as tooth 25.

Plate 68 also includes plate slot 63 and plate groove 65. The perimeter of plate slot 63 comprises plate groove 65. Plate groove 65 is defined by opposing track members 65*a* and 65*b* and by a plate groove face 65*c*. The configuration of plate groove 65 enables it to receive a portion of perimeter 40 of platform 30. As shown in FIG. 5, platform 30 is slidably and removably inserted in plate groove 65. Note that the width of platform 30 is substantially the same as the width of the space between the opposing sides of plate groove face 65*c*. While platform 30 and plate groove 65 can be designed to have a relatively close tolerance to ensure that platform 30 is securely held by the tight fit with plate groove 65 other mechanisms can also be utilized. For example, plate groove may have crimps, as shown at 65*d* in FIG. 4, which are very small portions of plate groove 65 wherein the opposing track members 65*a* and 65*b* are closer together than along the remainder of plate groove 65. Crimps 65*d* are intended to bind perimeter 40 of platform 30 into plate groove 65 so that platform 30 maintains its position in plate slot 63.

The assembly of the pieces shown in FIG. 4 is demonstrated in FIG. 5 while FIG. 6 is a cross sectional view of FIG. 5 taken along section line 6—6. FIGS. 5 and 6 are discussed together. In FIGS. 5 and 6, test piece 20 is placed on base 62. Platform 30 is inserted in plate slot 63 with perimeter 40 slidably and removably positioned in plate groove 65. Plate 68 is then connected to base 62 by inserting each post 64 through each corresponding plate aperture 67. Each retention nut 66 is then screwed onto each post 64 against spring discs 61. Test piece 20 is oriented such that outlet rim 36 of mold 34, as seen in FIG. 1 and FIG. 2, is directly above test piece 20. When clamping assembly 60 is tightened, outlet rim 36 will be firmly in contact with test piece 20, more particularly with dentin 27 of tooth 25. Note in FIG. 5 that test piece 20 is not securely held until clamping assembly 60 is tightened. This permits test piece 20 to be oriented so that outlet rim 36 is above the desired bonding site, which in this instance is a portion of dentin 27. For this purpose, platform 30 has front 44, as described above, which provides visual access to outlet rim 36 and test piece 20 as clamping assembly 60 is being tightened.

Once test piece 20 is properly oriented on base 62 and platform 30 is positioned in plate slot 63 and held in plate groove 65, retention nut 66 is tightened against disc springs 61 such that test piece 20 is securely and removably held in clamping assembly 60. Due to the light pressure applied to the top of plate 68 by disc springs 61, platform 30 does not flex or warp. In this position, mold 34 will not move relative to test piece 20 and the cylindrical shape of conduit 34 will not be deformed.

The purpose of perimeter support member 38 is evident at this point in FIGS. 5 and 6. Preferably, perimeter support member 38 and mold 34 extend downward from platform 30 an equal distance. Thus, as each retention nut 66 is being tightened, against disc springs 61, outlet rim 36 and perimeter support member 38 will touch top surface 23 of test piece 20 at the same time. As clamping assembly 60 is tightened, perimeter support member 38 prevents the interface between outlet rim 36 and test piece 20 from being changed due to the bowing of body 31. Accordingly, perimeter support member 38 prevents mold 34 from distorting or deforming and maintains the circular shape of outlet rim 36. While the platform can be used without a perimeter support member, the platform preferably has a perimeter support member to ensure that the shape of the mold is not distorted and remains cylindrical such that the resulting bond strength measurements are accurate. It is also possible to use the clamping assembly without disc springs 61. It is preferable, however, to use disc springs 61 as disc springs 61 ensure that uniform pressure is applied in each test. More particularly, disc springs 61 prevent over tightening of the assembly from occurring as over tightening can cause the bonding platform to warp. Perimeter support member 38 is an example of supporting means for bracing a platform on the top surface of a test piece.

Next, the method of forming adherend 10 and the bond between substrate 26 and restorative material 90 is described. After obtaining a test piece such as test piece 20 which already has a relatively flat and smooth top surface, then the top surface 23 of test piece 20 can be prepared as necessary. More specifically, the test sample or tooth 25 is prepared by first coating tooth 25 with a layer of etch and then rinsing the etchant off after the prescribed time. Second, a thin layer of primer and or adhesive is placed on the etched surface of tooth 25. Preparing test piece 20 includes any step necessary to replicate conditions where the bond is relied upon, such as a restorative material in a tooth. The steps discussed above such as priming and chemically etching at least a portion of a test piece are examples of different steps for preparing a test piece. The primers or adhesives are cured as discussed below, which is another step of preparing the test piece. Of course, flattening or grinding a substrate embedded in a holding material to yield a two component test piece, such as is shown at 20, is another example of a step necessary for preparing a test piece for use in a shear bond strength test.

After obtaining a clamping assembly and a test piece, then the clamp assembly is assembled as shown in FIGS. 4–6 with test piece 20 in position under platform 30. Before clamping assembly 60 is tightened, test piece 20 is moved around until conduit 39 is directly over the desired bonding site. The ability to select the location of the bonding site by moving test piece 20 relative to platform 30 held by clamping assembly 60 is very advantageous, particularly when the potential bond site is the dentin of a tooth. Many prior art systems do not permit such movement.

Once clamping assembly 60 is tightened with platform 30 and test piece 20 oriented such that outlet rim 36 is in contact with test piece 20, primers or adhesives on test piece 20 are light or chemical cured. More particularly, primers or adhesives visible through conduit 39 of mold 34 are cured. Platform 30 only permits the primers or adhesives visible through conduit 39 of mold 34 to be cured. Platform 30 prevents any excess primer from curing and prevents the formation of a "resin snowshoe" as the path of the curing light is blocked from the excess primer/adhesives by top surface 35 of platform 30. The presence of a "resin snowshoe" on top surface 23 would interfere with the measurement of the bond strength for reasons explained in reference to FIG. 11.

As indicated herein above, outlet end 42 is conical shaped to taper downward to form outlet rim 36. One of the functions of outlet end 42 is to prevent excess primer or adhesives, which are applied to top surface 23 of test piece 20, or more particularly the test sample, before composite material is bonded to bond site 22, from being pushed inside conduit 39. Note that if mold 34 did not have outlet rim 36, and conduit 39 terminated instead with a flat surface, then pressing mold 34 tightly against top surface 23 of test piece 20 might cause excess primer on top surface 23 to be pushed inside mold 34. Excessive primer or adhesive can result in capillary action causing the primer or adhesive to pool around the perimeter against conduit 39, thereby resulting in a defective test method. The shape of outlet end 42, particularly outlet rim 36, prevents this from occurring. Despite the foregoing, primer or adhesive can in some instances be delivered through mold 34, particularly when the primer or adhesive has a low viscosity.

Adherend 10 can be formed in mold 34 after preparing test piece 20 as needed, positioning test piece 20 and then securing test piece 20 in the desired position. To this end, FIG. 5 shows restorative material 90 being placed in conduit 39 of mold 34 via countersunk portion 32. Applicator 92 is representative of any means for delivering restorative material to a conduit of a mold. Conduit 39 is filled with restorative material 90 up to the desired level. Excess restorative material 90 is removed from countersunk portion 32 such that restorative material 90 is essentially in only conduit 39. As discussed above, mold 34 has a depth sufficient to permit or that does not prevent the curing light from curing all restorative material 90 inside of conduit 39. At this point, restorative material 90 inside conduit 39 is light or chemical cured and cylindrically shaped adherend 10 is formed. The curing of restorative tooth material 90 finalizes the formation of the bond between restorative material 90 and the substrate, tooth 25.

In the process of forming adherend 10, outlet rim 36 of mold 34 rests on the bonding substrate. More particularly when a two component test piece is used which includes a test sample such as a flattened tooth, then outlet rim 36 rests on the test sample. When forming adherend 10, outlet rim 36 is held securely against test piece 20 such that no hardenable material escapes from conduit 39 when conduit 39 is filled with hardenable material. The pointed shape of outlet rim 36 enhances its ability to prevent hardenable material from flowing out of conduit 39. The tight contact between test piece 20 and outlet rim 36 also ensures that the bottom end of adherend 10 is cylindrical in shape. Because the strength of the bond between test piece 20, particularly bond site 22, and adherend 10 is tested at the bottom end of adherend 10, the top surface of adherend 10 need not be necessarily flat. For this reason, excess composite material can be removed from countersunk portion 32 by any suitable device.

As indicated above, the pointed shape of outlet rim 36 combined with the ability of plate 68 to press platform 30 against test piece 20 as nuts 66 are tightened, provides a secure barrier against passage of the hardenable material out of conduit 39. So after selecting the location of the bonding site, platform 30, particularly outlet rim 36, also ensures that the hardenable material does not flow beyond the bond site. This ability of outlet rim 36 to tightly interface with test piece 20 and prevent restorative material from spilling out of conduit 39 ensures that flashing does not form around adherend 10. Overflow can skew test data in general.

After forming adherend 10, retention nuts 66 are loosened and plate 68 is lifted. The bond assembly, which is adherend 10 as bonded on test piece 20, is then disconnected from platform 30. This can be achieved by pushing on the top of adherend 10 with a suitable instrument while holding platform 30 or plate 68 or by pulling the bond assembly away from platform 30. The configuration of platform 30 ensures that the structure and position of the adherend is not altered when platform 30 is removed. Excess primer and adhesive on top surface 28 of test piece 20 may be removed as necessary.

Figure 7:
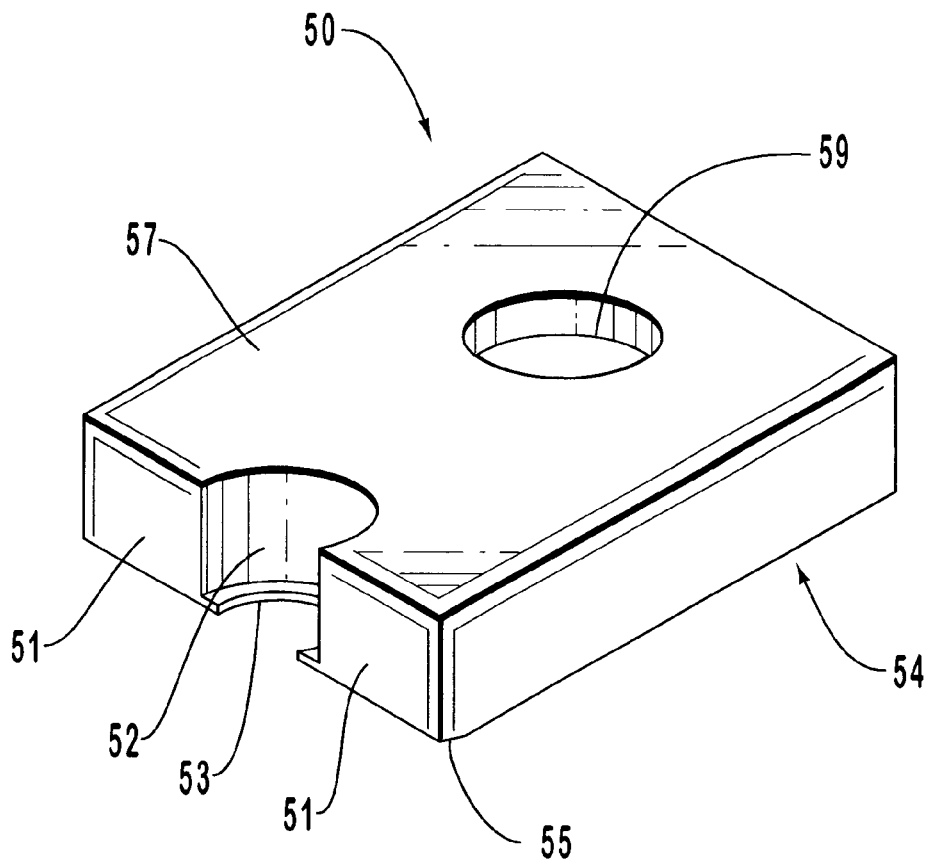
FIG. 7 is a perspective view of a crosshead.
Figure 8:
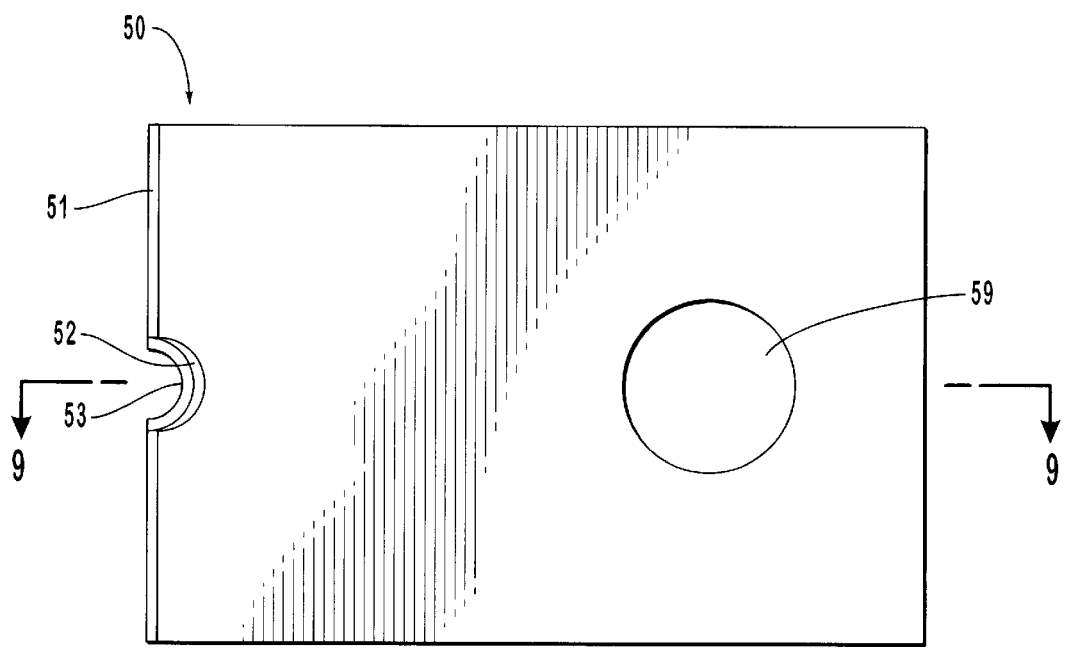
FIG. 8 is a top view of the crosshead.
Figure 9:
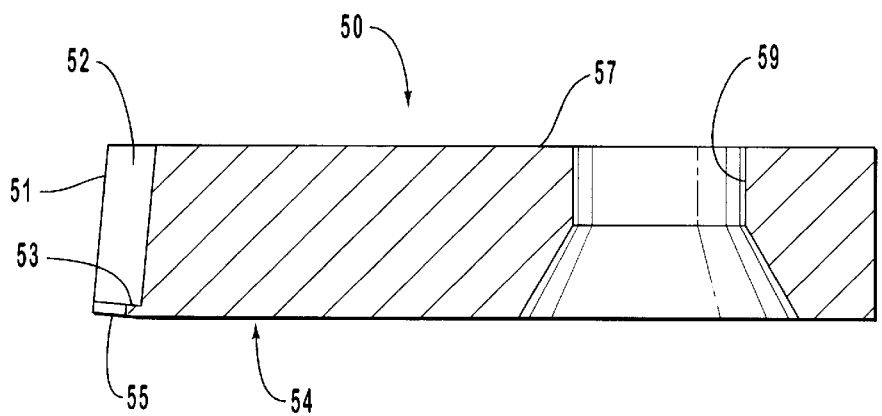
FIG. 9 is a cross-sectional view of the crosshead in FIG. 8, taken along the section line of 9—9 of FIG. 8.

FIGS. 7 through 11 illustrate methods and apparatus for shearing and testing the strength of a bond formed between adherend 10 and test piece 20. One embodiment of the present invention is a crosshead 50, illustrated in FIG. 7. FIG. 8 is a top view of crosshead 50 and FIG. 9 is a cross-sectional view of FIG. 8 along section line 9—9. FIGS. 7, 8 and 9 are discussed simultaneously.

The force required to shear adherend 10 from bond site 22 on test piece 20 with crosshead 50 is measured and recorded. Crosshead 50 is designed to push against the base of adherend 10 such that the measured force is the force required to shear adherend 10 from bond site 22 on test piece 20 rather than the force required to fracture or deform adherend 10.

The primary parts or surfaces of crosshead 50 include a top surface 57 opposite a bottom surface 54. At one end of bottom surface 54 is a contact surface 55 which slants up toward top surface 57 at a shallow angle. Contact surface 55 can angle up from bottom surface 54 at any degree which enables only contact surface 55 to contact a test piece during a bond strength test. For example, the angle may be about 5°. As described in greater detail herein below, this configuration as well as the design of the embodiment shown in FIGS. 12–16, enable only contact surface 55 to contact and rest flush on the test piece.

Crosshead 50 has a face 5 that extends between contact surface 55 and top surface 57. Crosshead 50 also has an aperture 59 used to attach crosshead 50 to a particular device or arm 80 which provides the shearing force. Crosshead 50 must be mounted to arm 80 at an angle where contact surface 55 would be able to be aligned parallel to top surface 23 of test piece 20.

Contact surface 55 has a groove 52 cut into it which extends perpendicularly from contact surface 55 through to top surface 57 such that groove 52 is visible in its entirety in face 51 which extends between contact surface 55 and a top surface 57. Although, groove 52 preferably has a semicircular shape as shown, it may also have other configurations. Groove 52 has a top end at top surface 57 and a bottom end at contact surface 55. Groove 52 is an example of groove means for receiving an adherend.

At the bottom end of groove 52, where it meets contact surface 55, is a section which has a slightly smaller radius than the majority of groove 52. This smaller diameter section creates a lip 53 which extends inward from groove 52. The front or inside radius of lip 53 is also perpendicular to contact surface 55. The configuration and size of lip 53 relative to groove 52 enables an adherend to be sheared from a bond site due to contact from lip 53 and not due to other structures such as groove 52. While the lip is shown having a semicircular configuration, it may have any configuration corresponding with that of the groove. More particularly, the lip is sized and shaped to correspond with the size and shape of the adherend while the groove is complimentary to this shape and slightly larger in dimensions. Lip 53 is an example of means for contacting an adherend to shear the adherend from the bond site on the test piece when the crosshead is pushed against an adherend.

Figure 10:
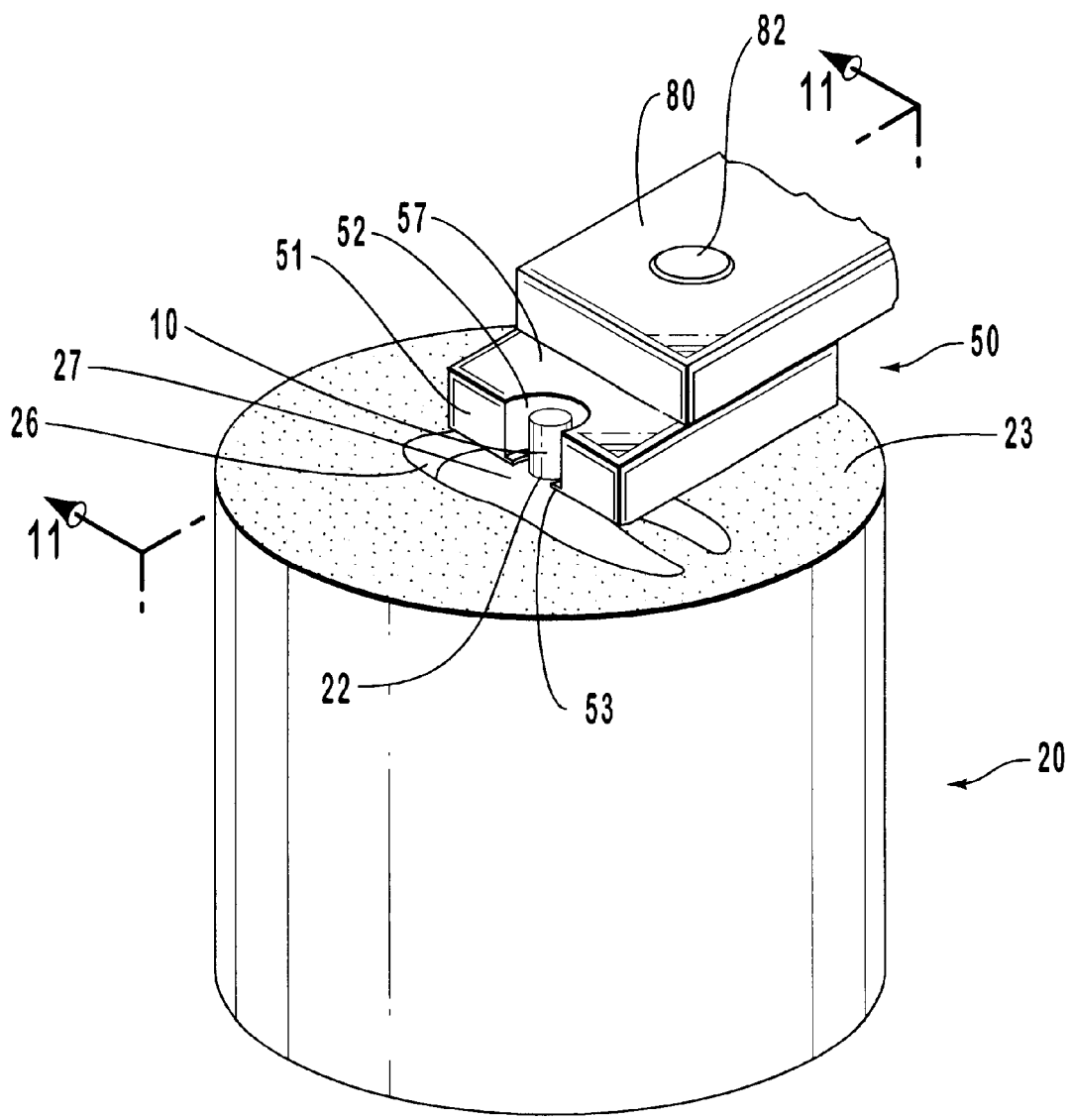
FIG. 10 is a perspective view a crosshead positioned to shear an adherend from the top surface of a test sample embedded in a test piece.
Figure 11:
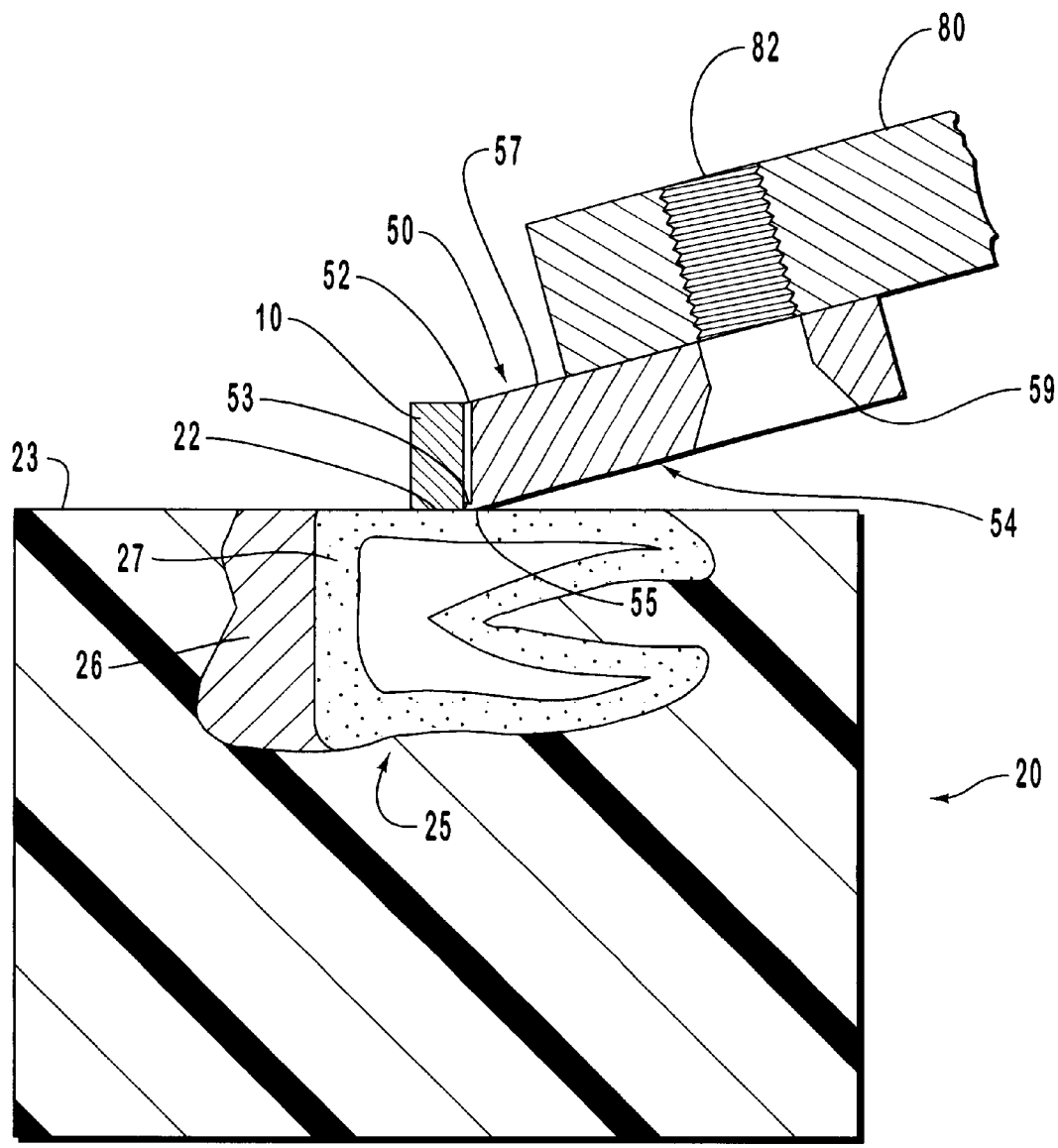
FIG. 11 is a cross-sectional view of FIG. 10 taken along the section line of 11—11 of FIG. 10.
Figure 12:
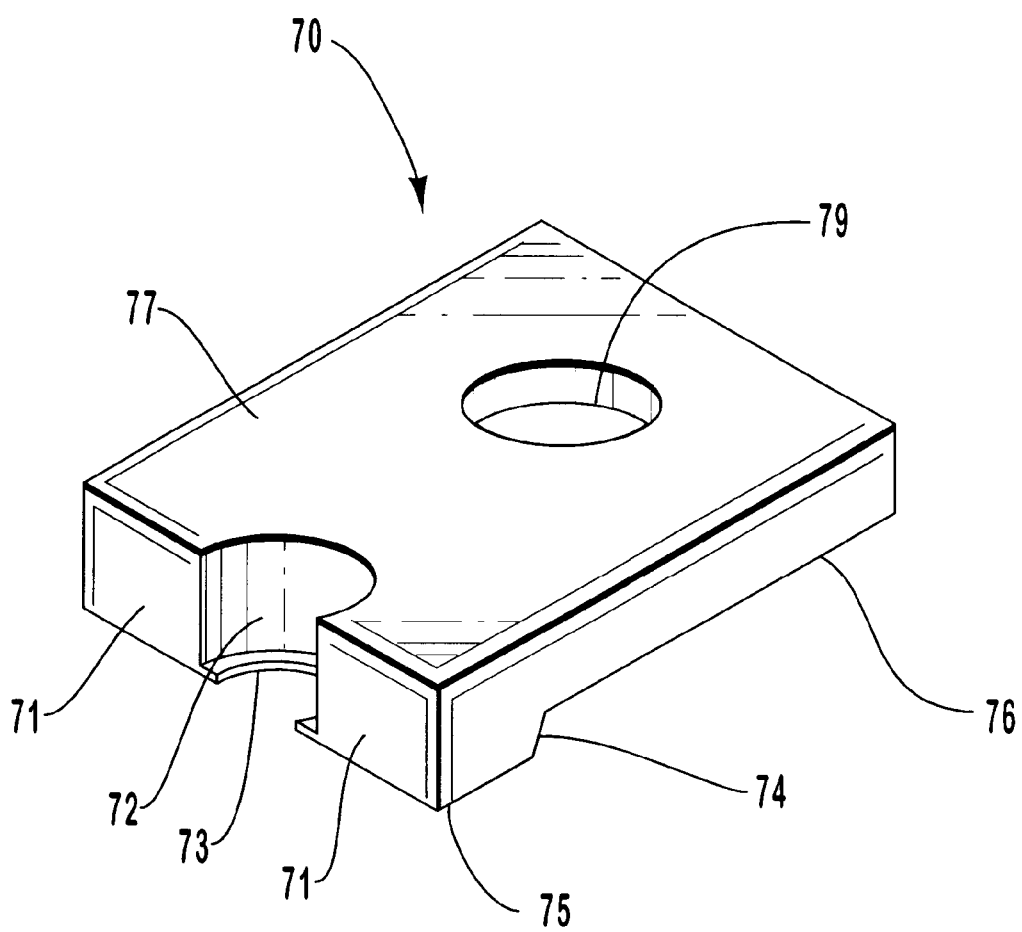
FIG. 12 is a perspective view of another embodiment of a crosshead.
Figure 13:
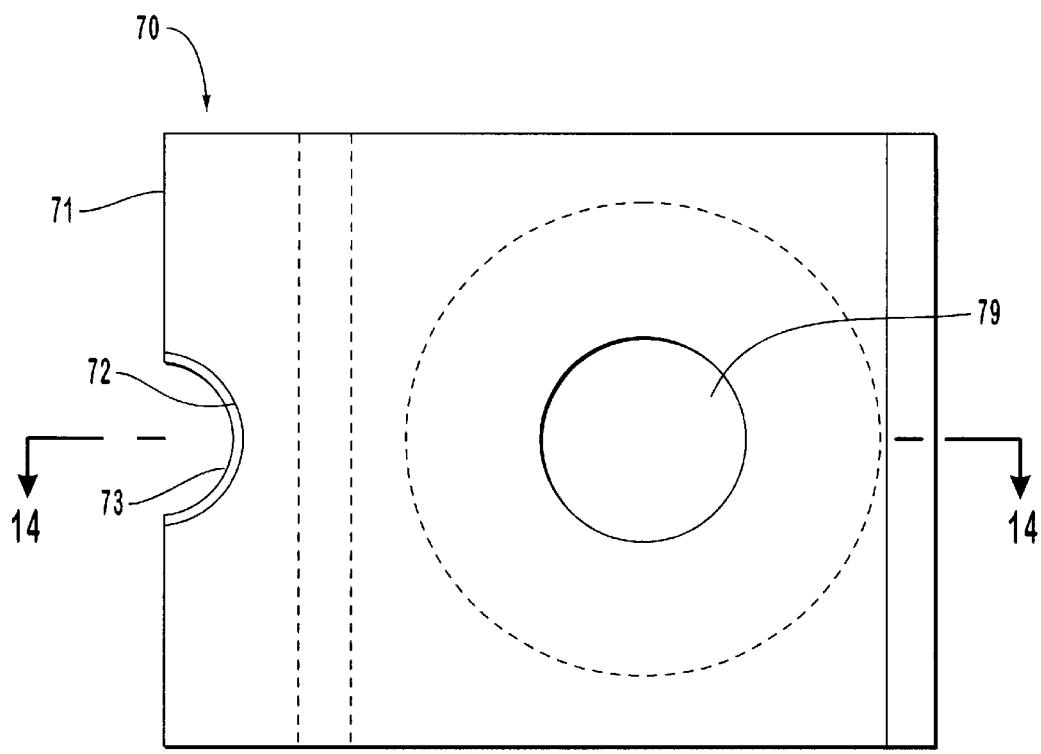
FIG. 13 is a top view of the crosshead shown in FIG. 12.
Figure 14:
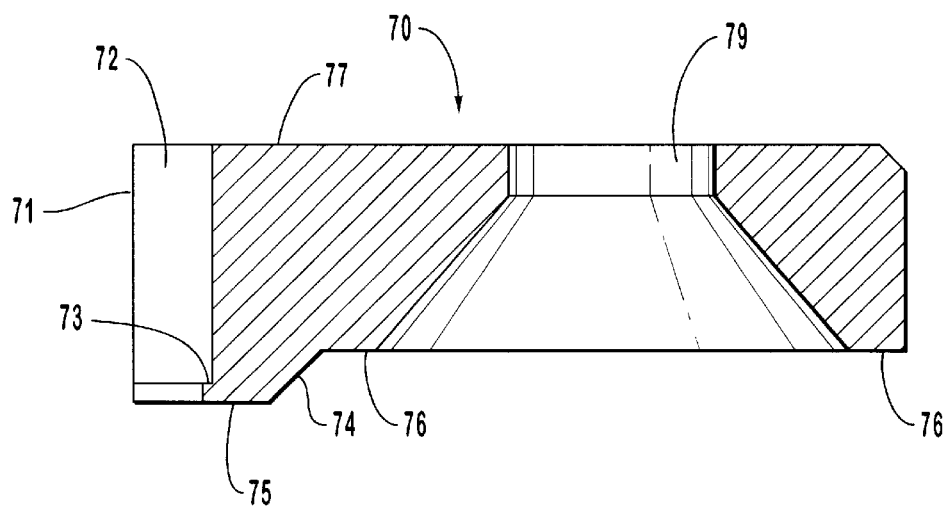
FIG. 14 is a cross-sectional view of the crosshead in FIG. 13, taken along the section line of 14—14 of FIG. 13.
Figure 15:
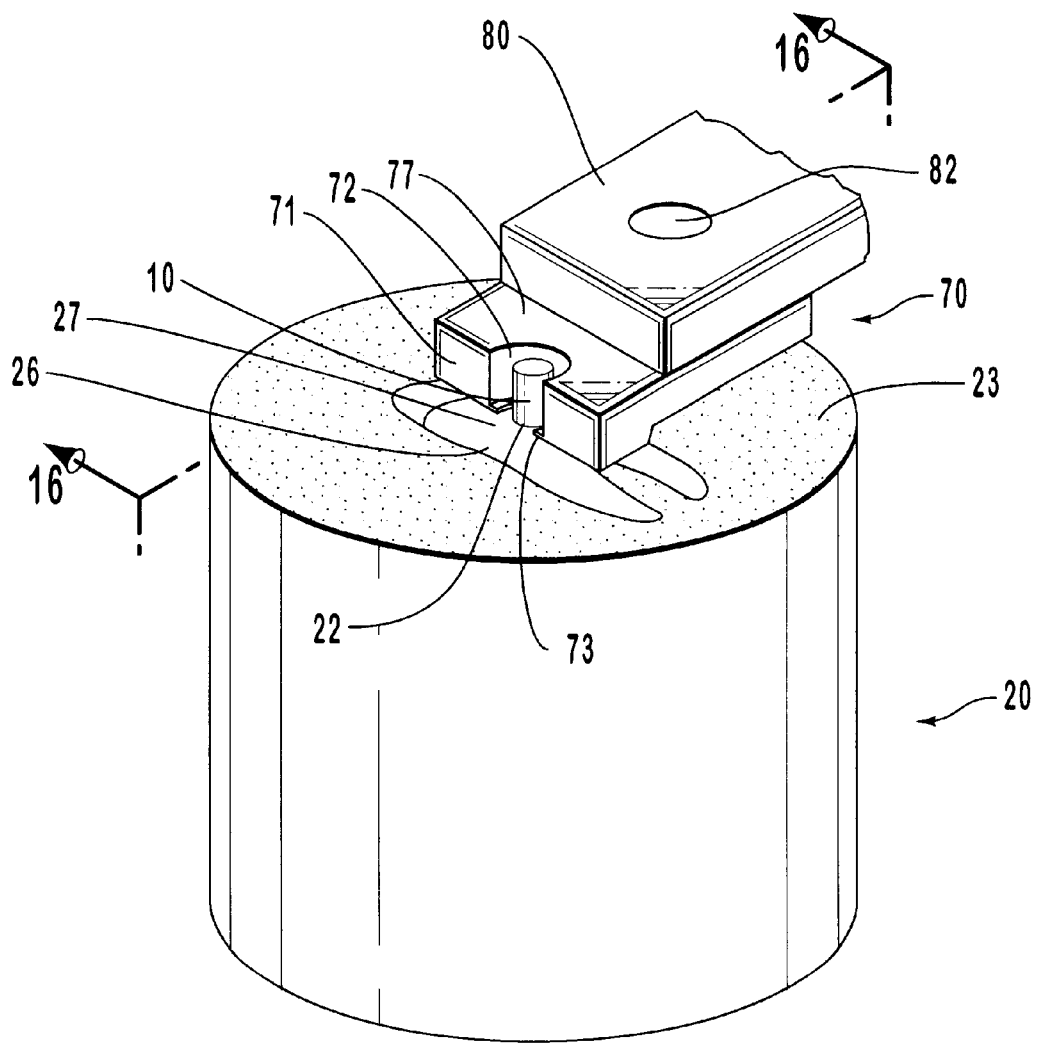
FIG. 15 is a perspective view the crosshead shown in FIG. 12 positioned to shear an adherend from the top surface of a test sample embedded in a test piece.

The functions of the parts of crosshead 50 are described in relation to FIGS. 10 and 11. FIG. 10 is perspective view of crosshead 50 positioned to test the strength of a bond between adherend 10 and bond site 22 on a test piece 20. FIG. 11 is a cross-sectional view of FIG. 10 taken along section line 11—11 and illustrates lip 53 pushing against the base of adherend 10.

Arm 80 is representative of any device capable of connecting to crosshead 50 such that crosshead 50 can be moved to shear adherend 10 from test piece 20 or more particularly from dentin 27 of tooth 25, which is embedded in holding material 28. To test the strength of a bond, crosshead 50 is oriented such that contact surface portion 55 is flush with top surface 23 of test piece 20. Contact surface portion 55 is aligned such that when contact surface portion 55 is flush with top surface 23, groove 52 and lip 53 are essentially perpendicular to top surface 23. This permits lip 53 to push directly against the base of adherend 10 and prevents groove 52 from pushing against the top of adherend 10. If groove 52 were to push against adherend 10, there would be an increased likelihood that adherend 10 would fracture rather than test the adhesive. More particularly, if adherend 10 were pushed at the top, adherend 10 is likely to break rather than the adhesive. Because pushing at the base of adherend 10 with lip 53 prevents adherend 10 from being used as a lever, a more accurate measurement of the bond strength can be taken. Lip 53 also has a thickness suitable to prevent lip 53 from fracturing adherend 10.

Only lip 53 contacts adherend 10 and pushes against the base of adherend 10. If groove 52 did not have a larger diameter than lip 53 then groove 52 would contact adherend 10. As indicated herein above, excessive contact between groove 52 and adherend 10 would enable groove 52 to lever or push or adherend 10 and any measurement of the bond strength would be skewed accordingly.

Contact surface portion 55 also helps to minimize the amount of surface area of crosshead 50 in contact with test piece 20 such that the force of friction is minimized as the strength of the bond between adherend 10 and test piece 20 is tested. Also when contact between crosshead 50 and top surface 23 is minimized there is less opportunity for obstructions to hinder placing contact surface 55 flush with top surface 23. Once crosshead 50 is oriented correctly, a vertical force is applied until adherend 10 is sheared from bond site 22 of test piece 20. The strength of this force is measured and recorded.

Note that arm 80 is coupled to crosshead 50 by screw 82 in aperture 59. Aperture 59 is an example of attachment means for attaching a crosshead to an arm. Arm 80 is an example of pushing means for pushing a crosshead vertically against an adherend to shear the adherend from a test piece.

FIGS. 12–16 depict another embodiment of a crosshead identified at 70. FIGS. 12–16 respectively depict crosshead 70 in the same views as crosshead 50 is depicted in FIGS. 7–11.

Crosshead 70 has essentially the same parts as crosshead 50 however the configurations differ. Crosshead 70 has a face 71, which extends between a contact surface 75 and a top surface 77. Crosshead 70 also has an aperture 79 used to attach crosshead 70 to a particular device which provides the shearing force, such as arm 80.

Contact surface 75 is offset but parallel to bottom surface 76 and is connected to bottom surface 76 by connecting surface 74. Having contact surface 75 offset from bottom surface 76 accomplishes the same thing for crosshead 70 that contact surface 55 being at an offset angle from bottom surface 54 does for crosshead 50; namely this allows for only the contact surfaces of these crossheads to be in contact with top surface 23 of test piece 20 during testing.

Contact surface 75 also had a groove 72 cut into it which extends perpendicularly from contact surface 75 through to top surface 77 such that groove 72 is visible in its entirety in face 71. Groove 72 preferably has a semicircular shape like groove 52 and is another example of a groove means. A lip 73 is located at the bottom end of groove 72 which extends out from beyond the bottom end of groove 72 as groove 72 has a slightly larger radius than lip 73. Lip 73 is another example of a means for contacting an adherend to shear the adherend from the bond site on a test piece.

Face 71, groove 72, and lip 73 are all substantially perpendicular with top surface 77 and bottom surface 76. In contrast to the configuration of contact surface 55, groove 52 and lip 53 of crosshead 50, it is unnecessary for contact surface 75 and groove 72 to be angled due to contact surface 75 being offset from bottom surface 76, as described below.

Bottom surface 76 is recessed but perpendicular to contact surface portion 75, which is configured to rest flush on the top surface of a test piece and for movement or sliding on the test piece as lip 73 is urged against an adherend. Bottom surface 76 is recessed from contact surface 75 to minimize contact of crosshead 70 to top surface 23 of a test piece 20. This minimizes friction and allows for flush placement of contact surface 75 so that shear forces are applied to adherend 10 rather than leverage forces as would be the case if crosshead 70 were obstructed from being placed directly against top surface 23. The offset from flat section 76 and contact surface portion 75 is typically about 0.025 inches.

Figure 16:
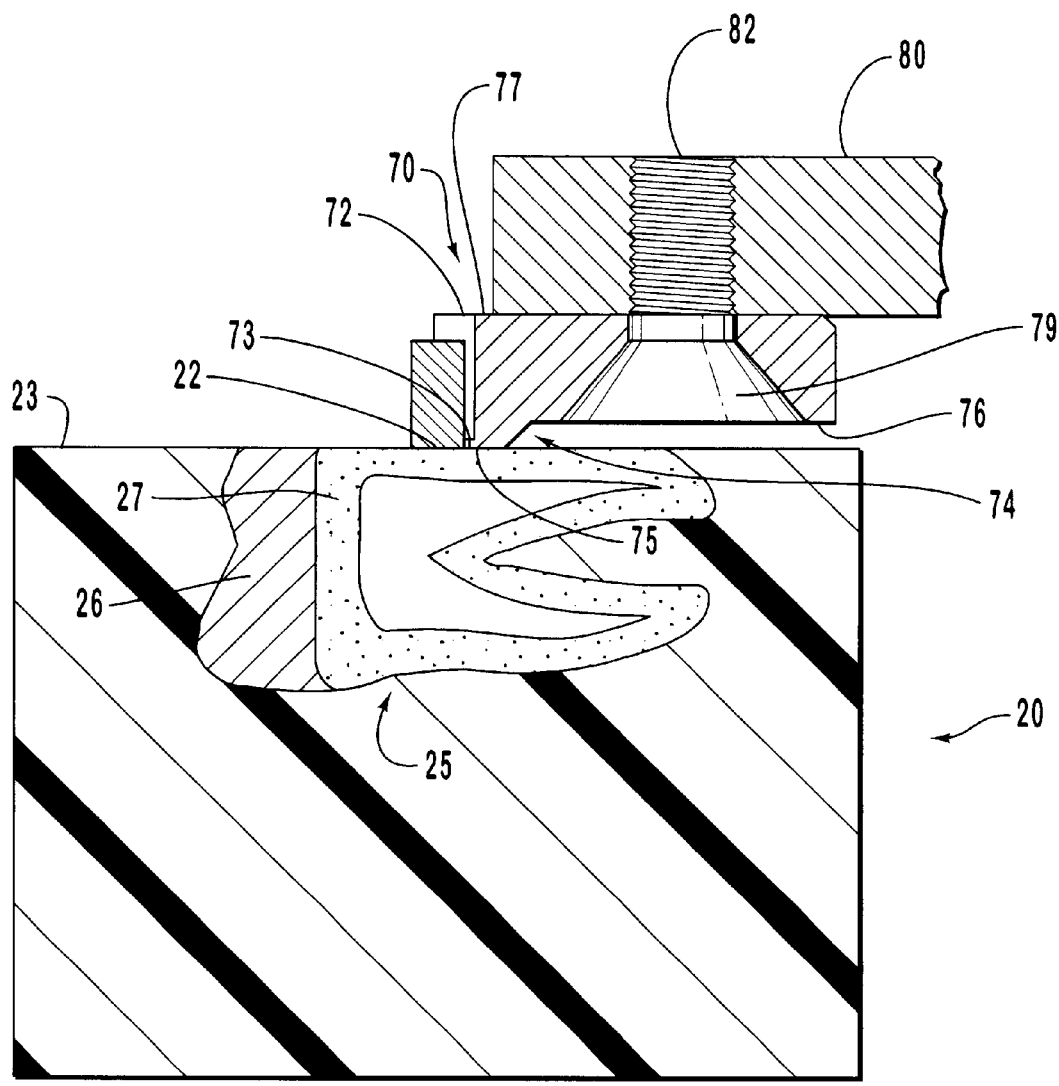
FIG. 16 is a cross-sectional view of FIG. 15 taken along the section line of 16—16 of FIG. 15.

As shown in FIG. 16, the configuration of contact surface 75 enables crosshead 70 to approach and contact an adherend with bottom surface 76 essentially parallel to the top surface 23 of test piece 20 as well as top surface 77. Additionally, groove 72 is essentially parallel to adherend 10. By resting contact surface portion 75 on top surface 23, it is virtually impossible for groove 72 to contact adherend 10 which is similar to the function of crosshead 50. More particularly, the configuration of crosshead 50 requires that crosshead 50 be attached to arm 80 at an angle to allow contact surface 55 to be placed parallel to top surface 23 and to allow groove 52 and lip 53 to be parallel to adherend 10. With crosshead 70, the same alignment to adherend 10 and top surface 23 are accomplished but without the angles involved with crosshead 50. This makes crosshead 70 much easier for machinists to fabricate because basically all of its surfaces are parallel or at right angles to each other. These crossheads are preferably made of hardened steel to reduce deformation and wear.

Note that in another embodiment, the crosshead is similar to that shown at 70 except the bottom surface and the contact surface are not offset with respect to each other such that there is a single flat surface. In such an embodiment, it may be necessary to identify the effect of friction and misalignment or leverage forces to correctly determine the bond strength.

In review, some advantages of the features of the platform and the crosshead are described herein below. Platform 30 illustrated in FIGS. 2 and 3 increases the likelihood of obtaining an accurate bond strength measurement for numerous reasons. First, platform 30 prevents the formation of a resin snowshoe. If a resin snowshoe is formed, then the bond tested is not between adherend 10 and bond site 22, but between adherend 10 and more surface area of test piece 20. Platform 30 ensures that the bond does not extend beyond the area within mold 34 of platform 30. The configuration of conduit 39 yields a cylindrically shaped adherend 10. Perimeter support member 38 prevents body 31 of platform 30 from bowing and thereby distorting the shape of adherend 10. Front 44 of platform 30 provides visibility to the interface between outlet rim 36 and test piece 20 to ensure proper placement of the bond. Body 31 prevents the curing light from curing the excess primer/adhesives thereby eliminating the formation of a resin snowshoe. Outlet rim 36 allows for better isolation and less displacement of adhesives upon placement of platform 30.

Crosshead 50, illustrated in FIGS. 7 through 11, and crosshead 70 in FIGS. 12–16 also increases the likelihood of obtaining an accurate bond strength measurement. First, contact surface portion 55 or 75 reduces the force of friction by limiting the amount of surface area of the bottom surface of the crosshead that is in contact with top surface 23 of test piece 20. Second, lip 53 or 73 pushes against adherend 10 at a point near the bond between adherend 10 and test piece 20. Third, the lip has a thickness sufficient to load adherend 10 without fracturing or levering it from test piece 20. Fourth, the groove 52 or 72 is larger than the lip such that contact is prevented between adherend 10 and the groove when the crosshead is positioned or oriented to shear adherend 10 from test piece 20. Fifth, the lip has the same essentially the same diameter as adherend 10 and is a means of distributing the applied test load over the base of adherend 10 such that adherend 10 is not fractured. If the lip was not present, then a very small point of contact would be made as a straight line contacted adherend 10 thus increasing the likelihood of fracturing adherend 10. Sixth, the contact surface portion facilitates easy alignment of crosshead 50 to be parallel and flush with surface 23 of test piece 20, particularly contact surface portion 75.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes, which come within the meaning and range of equivalency of the claims, are to be embraced within their scope.

What is claimed and desired to be secured by United States Letters Patent is:

1. An improved crosshead for use in an apparatus for shearing an adherend from a bond site of a test piece and for measuring bond strength between the adherend and the bond site when shearing the adherend, the crosshead comprising:
   a top surface and an opposing bottom surface;
   the bottom surface comprising a contact surface which minimizes the portion of the bottom surface that comes into contact with the test piece when shearing the adherend;
   a lip formed on the contact surface which substantially conforms to the shape of the adherend and which minimally contacts the adherend near the bottom thereof in order and apply the desired shear force when testing the bond strength.

2. A crosshead as defined in claim 1, wherein said lip is formed at the bottom end of the groove means, and wherein the groove means and the lip are semicircular shaped, and wherein the groove means has a larger radius than the lip.

3. A crosshead as defined in claim 1, wherein when the contact surface is flush on the test piece, the groove means is perpendicular to the bond site of the test piece.

4. A crosshead as defined in claim 1, wherein the groove means and lip are at 90° with respect to the top surface of the crosshead.

5. A crosshead as defined in claim 1, wherein the lip extends out from the bottom end of the groove means while having substantially the same shape as the groove means.

6. An improved crosshead for use in an apparatus for shearing an adherend from a bond site of a test piece and for measuring bond strength between the adherend and the bond site when shearing the adherend, the crosshead comprising:
   a top surface and a bottom surface comprising a contact surface, with a face extending between the contact surface and the top surface, the contact surface minimizing the portion of the bottom surface that comes into contact with the test piece when shearing the adherend;
   a groove formed in the face which extends between the top surface and the contact surface, the groove having a top end and a bottom end, the groove being configured to receive the adherend;
   a lip extending from the bottom end of the groove while having substantially the same shape as the groove, such that by using the lip to contact the adherend while the contact surface is flush on the test piece enables the adherend to be sheared from the bond site.

7. A crosshead as defined in claim 6, wherein the crosshead has a bottom surface opposite the top surface which is configured to avoid contacting the test piece as the crosshead is pushed against the adherend on the test piece.

8. A crosshead as defined in claim 6, wherein the groove has a size such that the groove does not contact the adherend when the contact surface is flush on the test piece.

9. A crosshead as defined in claim 6, wherein the crosshead is configured such that when the contact surface is flush on the test piece, the groove is perpendicular to the bond site of the test piece.

10. A crosshead as defined in claim 6, wherein the groove and lip are at 90° with respect to the contact surface.

11. A crosshead as defined in claim 6, wherein the groove, lip and face are perpendicular to the contact surface of the crosshead.

12. A crosshead as in claim 6, wherein the lip is sized and shaped to correspond with the size and shape of the adherend.

13. An improved crosshead for use in an apparatus for shearing an adherend from a bond site of a test piece and for measuring bond strength between the adherend and the bond site when shearing the adherend, the crosshead comprising:
   a top surface and an opposing bottom surface;
   the bottom surface comprising a contact surface which minimizes the portion of the bottom surface that comes into contact with the test piece when shearing the adherend;
   a face extending between the top surface and the contact surface;
   a groove formed in the face which extends between the top surface and the contact surface, the groove having a top end and a bottom end, the groove being configured to receive the adherend; and
   a lip extending from the bottom end of the groove while having substantially the same shape as the groove, such that by using the lip to contact the adherend while the contact surface is flush on the test piece enables the adherend to be sheared from the bond site.

14. A crosshead as defined in claim 13, wherein the crosshead is configured such that when the contact surface is flush on the test piece, the groove is perpendicular to the bond site of the test piece.

15. A crosshead as defined in claim 13, wherein the groove and lip are at 90° with respect to the contact surface.

16. A crosshead as in claim 13, wherein the contact surface and the bottom portion are offset about 0.025 inches from each other.

17. A crosshead as in claim 13, wherein the lip is sized and shaped to correspond with the size and shape of the adherend.

18. A method of using an improved crosshead in an apparatus for shearing an adherend from a test piece and for measuring the strength of the bond between the adherend and a bond site on the test piece when shearing the adherend, the method comprising:

a step for bonding the adherend to the bond site of the test piece;

an act of preparing the crosshead so that i) it has a contact surface at its bottom which will serve to minimize contact between the test piece and the crosshead, and so that ii) it has a contact lip on its front which will serve to minimize contact between the adherend, and so that iii) it has a groove means for receiving the adherend, the groove means being located in the face and extending between the top surface and the contact surface, the groove means having a top end and a bottom end, wherein the groove means is a semicircular depression the crosshead;

a step for placing the crosshead adjacent to the adherend in preparation for exerting a shear force to the adherend;

a step for exerting sufficient shear force to the crosshead to shear the adherend from the bond site; and a step for measuring the exerted shear force.

* * * * *

UNITED STATES PATENT AND TRADEMARK OFFICE
CERTIFICATE OF CORRECTION

PATENT NO.  : 6,324,916 B1                                Page 1 of 1
DATED       : December 4, 2001
INVENTOR(S) : Neil T. Jessop It is certified that error appears in the above-identified patent and that said Letters Patent is hereby corrected as shown below:

<u>Column 12,</u>
Line 26, change "5" to -- 51 --

Signed and Sealed this

Fourteenth Day of May, 2002

Attest:

Attesting Officer

JAMES E. ROGAN
Director of the United States Patent and Trademark Office